United States Patent [19]

Hill

[11] 4,117,225
[45] Sep. 26, 1978

[54] PROCESS FOR THE PREPARATION OF 1-DIPHENYLMETHYL-4-(6-METHYL-2-PYRIDYLMETHYLENEAMINO)PIPERAZINE

[75] Inventor: John B. Hill, Woodstock, Ill.

[73] Assignee: G.D. Searle & Co., Chicago, Ill.

[21] Appl. No.: 812,019

[22] Filed: Jun. 30, 1977

[51] Int. Cl.² .................. C07D 401/12; C07D 295/00
[52] U.S. Cl. .................................... 542/425; 542/420; 544/360; 560/36; 560/171; 260/239 BC
[58] Field of Search ..................... 260/268 N; 542/425

[56] References Cited

U.S. PATENT DOCUMENTS

| 3,178,422 | 4/1965 | Cusic et al. | 542/425 |
| 3,183,229 | 5/1965 | Cusic et al. | 542/425 |

FOREIGN PATENT DOCUMENTS 984,704  3/1965  United Kingdom ............... 542/425

Primary Examiner—Allen B. Curtis
Attorney, Agent, or Firm—Joy A. Serauskas

[57] ABSTRACT

A new process utilizing certain novel intermediates for the preparation of 1-diphenylmethyl-4-(6-methyl-2-pyridylmethyleneamino)piperazine is described herein. The process utilizes readily available starting material and has the distinct advantage of having no N-nitroso intermediate in its procedure.

1 Claim, No Drawings

PROCESS FOR THE PREPARATION OF 1-DIPHENYLMETHYL-4-(6-METHYL-2-PYRIDYL-METHYLENEAMINO)PIPERAZINE

1-Diphenylmethyl-4-(6-methyl-2-pyridylmethyleneamino)-piperazine which is described in U.S. Pat. No. 3,183,229 is a water insoluble benzhydrylpiperazine derivative that possesses pharmacological utility. Specifically, this compound possesses utility as a potent anti-convulsant agent.

This utility is evidenced by the following procedure which is a modification of the procedure described by E. A. Swinyard et al., J. Pharmacol. Exp. Therap., 106, 319(1952). This procedure reads as follows. 50 Mg per kg. of the compound to be tested, dissolved or suspended in 10 ml of a vehicle such as saline or corn oil, is administered intragastrically to each of 10 mice. At a specific time after the administration of the test compound (ordinarily 2½ hours), each mouse is challenged with a current of 50 mA, delivered via corneal electrodes, for 0.2 seconds. This current is sufficient to induce maximal electroshock seizures in 100% of control animals. A compound is considered active in this test if the hind limb tonic extensor component of the seizure pattern is abolished in at least 20% of the animals in the group to which the compound is administered.

1-Diphenylmethyl-4-(6-methyl-2-pyridylmethyleneamino)piperazine had an $ED_{50}$ of 7.8 mg/kg and diphenylhydantoin — a known anticonvulsant agent — had an $ED_{50}$ of 6.8 mg/kg when tested for anticonvulsant activity two and one-half hours following intragastric administration in the above-mentioned procedure.

A known procedure which is described in U.S. Pat. No. 3,183,229, for the preparation of 1-diphenylmethyl-4-(6-methyl-2-pyridylmethyleneamino)piperazine proceeds through an N-nitroso intermediate — 1-diphenylmethyl-4-nitrosopiperazine.

A major and growing concern among scientists is the evidence that certain types of compounds exhibit carcinogenic activity when tested in animals. Among these suspect compounds are nitroso compounds such as p-nitrosodimethylaniline and N,4-dinitroso-N-methylaniline. These compounds when tested in animals showed some carcinogenic activity (see *Dangerous Properties of Industrial Materials* - Fourth Edition by N. Swing Sax - p 283–284). Even though it certainly can not be inferred from this data that all nitroso compounds would exhibit carcinogenic activity, it would seem reasonable that a procedure for the preparation of a pharmaceutical agent which would avoid an N-nitroso intermediate would be of definite use because of the undesirable light cast upon N-nitroso compounds in general by such data.

It is the object of the present invention to provide a useful procedure for the preparation of 1-diphenylmethyl-4-(6-methyl-2-pyridylmethyleneamino)piperazine which does not have any N-nitroso intermediates. It is a further object of this invention to provide certain novel intermediates useful in the process of this invention.

The process of the present invention is illustrated by the following Scheme A

Scheme A

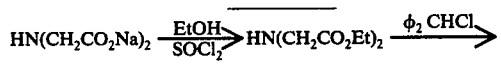

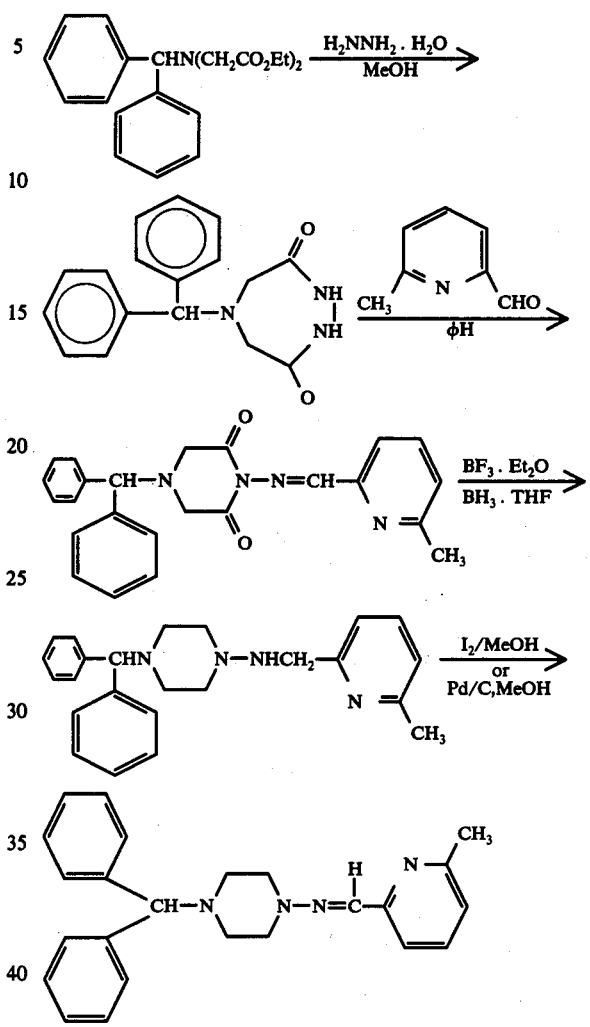

By way of illustration, the first step of Scheme A is shown. Iminodiacetic acid, disodium salt monohydrate is reacted with thionyl chloride to give diethyliminodiacetate. This reaction is conducted in ethanol. Time and temperature are not deemed critical to the conduct of this reaction. Time varies from 20 hrs. to 72 hrs. depending on the particular temperature employed. The resulting product from the first step — diethyliminodiacetate — is then treated with chlorodiphenylmethane. Time and temperature are typically in the range of 24 hrs. to 72 hrs. and 70°–150° C. This reaction is typically carried out at a temperature of 70°–80° C for 72 hrs. to afford diethyl-N-benzhydryliminodiacetate. Treatment of diethyl-N-benzhydryliminoacetate with hydrazine hydrate affords 5-diphenylmethyl-3,7-diketo-1,2-dihydro-1,2,5-triazepine. This reaction is conveniently carried out in the presence of methanol. Typically this reaction is carried out at reflux and a reaction time of 20 hrs. Treatment of 5-diphenylmethyl-3,7-diketo-1,2-dihydro-1,2,5-triazepine with 6-methylpyridine-2-carboxaldehyde affords 1-diphenylmethyl-4-(6-methyl-2-pyridylmethyleneamino)-3,5-diketopiperazine. This reaction is carried out in the presence of a solvent, a preferred solvent being benzene or toluene. Time and temperature are not critical, with reflux temperature and reaction time of 4 hours being typical. Reduction of the ketone groups on the piperazine ring is effected by the treatment of 1-diphenylmethyl-4-(6-methyl-2-pyridylmethyleneamino)-3,5-diketopiperazine with a mixture of diborane in tetrahydrofuran and boron trifluoride in diethyl ether. This procedure affords 1-diphenylmethyl-4-(6-methyl-2-pyridylmethylamino)piperazine. 1-Diphenylmethyl-4-(6-methyl-2-pyridylmethylamino)piperazine is then treated with 0.1M iodine/MeOH to afford the dehydrogenated product — 1-diphenylmethyl-4-(6-methyl-2-pyridylmethyleneamino)piperazine. Dehydrogenation of 1-diphenylmethyl-4-(6-methyl-2-pyridylmethylamino)-piperazine can also be accomplished using palladium-on-carbon in the presence of methanol in place of 0.1M iodine/MeOH reagent.

Scheme A illustrates the preparation of 1-diphenylmethyl-4-(6-methyl-2-pyridylmethyleneamino) piperazine - a compound in which there is no substitution on the phenyl rings of the diphenylmethyl moiety. It would be obvious to one skilled in the art that Scheme A would also serve to illustrate the preparation of compounds in which the phenyl rings of the diphenylmethyl moiety could be substituted by different groups such as alkyls or halogens.

The following examples describe in detail the preparation of compounds utilizing the process of the present invention. It will be apparent to those skilled in the art that many modifications, both of materials and method, may be practiced without departing from the purpose and intent of this disclosure. Throughout the examples hereinafter set forth, temperatures are given in degrees Centigrade (° C.) and relative amounts in parts by weight, except as otherwise noted.

EXAMPLE 1

132 Parts by weight of iminodiacetic acid disodium salt monohydrate and 403 parts by weight of thionyl chloride in the presence of 500 parts by volume of ethanol are heated at reflux for 20 hrs. The solvent is then stripped off and the resulting residue is dissolved in water. The aqueous solution is basified with sodium hydroxide until a pH of 8.5 is reached. This acidified solution is extracted with methylene chloride and the resulting extract is dried over a drying agent. Evaporation of the extract to dryness affords as an oil diethyliminodiacetate.

EXAMPLE 2

A mixture of 98 parts by weight of diethyliminodiacetate and 47.8 parts by weight of benzhydryl chloride is heated at a temperature between 70°-80° C for 72 hrs. This mixture is then dissolved in benzene and the resulting solution is first washed with 3N hydrochloric acid, then water and then dried over a drying agent. Evaporation of this solution to dryness affords as an oil diethyl-N-benzhydryliminodiacetate.

EXAMPLE 3

106 Parts by weight of diethyl-N-benzhydryliminodiacetate and 100 parts by weight of hydrazine hydrate in the presence of 300 parts by volume of methanol are heated at reflux for 20 hrs. The solvent is removed and the resulting residue is dissolved in water. Acidification of this aqueous solution with 3N hydrochloric acid results in the formation of precipitate which is filtered off. This precipitate is 5-diphenylmethyl-3,7-diketo-1,2-dihydro-1,2,5-triazepine, melting at 171°-173° C. This compound is represented by the following structural formula

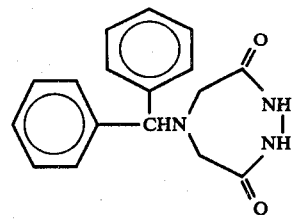

EXAMPLE 4

A mixture of 22.6 parts by weight of 6-methylpyridine-2-carboxaldehyde and 50 parts by weight of 5-diphenylmethyl-3,7-diketo-1,2-dihydro-1,2,5-triazepine in the presence of 800 parts by volume of benzene is heated at reflux temperature for 4 hrs. with continuous water separation. The mixture is first washed with 3N hydrochloric acid, then washed with water and evaporated to dryness to give a residue. Crystallization of this residue from ethanol affords 1-diphenylmethyl-4-(6-methyl-2-pyridylmethyleneamino)-3,5-diketopiperazine melting at 161°-163° C. This compound is represented by the following structural formula

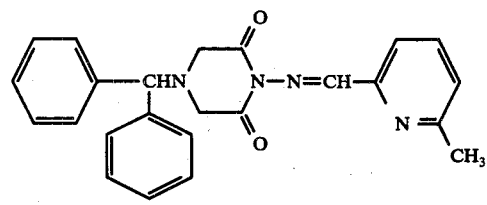

EXAMPLE 5

20 Parts by volume of 1M diborane in tetrahydrofuran is added at 0° C to 4.0 parts by weight of 1-diphenylmethyl-4-(6-methyl-2-pyridylmethyleneamino)-3,5-diketopiperazine and 1.4 parts by weight of boron trifluoride diethylether in 100 parts by volume of tetrahydrofuran. This mixture is stirred at ambient temperature for 18 hrs. 6N Hydrochloric acid is now added and tetrahydrofuran is evaporated. The resulting aqueous solution is extracted with methylene chloride. The methylene chloride extract is then dried over a drying agent. Evaporation of the solvent affords as an oil 1-diphenylmethyl-4-(6-methyl-2-pyridyl-methylamino) piperazine.

EXAMPLE 6

To 4.25 parts by weight of 1-diphenylmethyl-4-(6-methyl-2-pyridyl-methylamino)piperazine in the presence of 750 parts by volume of methanol under nitrogen is added 110 parts by volume of 0.1M iodine/methanol. This mixture is stirred for 15 mins. and then treated with sodium thiosulfate and 20% aqueous solution of sodium hydroxide. The mixture is then extracted with methylene chloride, and the extract is dried over a drying agent. Evaporation of the solvent gives an oil. Crystallization of this oil from ethyl ether affords 1-diphenylmethyl-4-(6-methyl-2-pyridylmethyleneamino)piperazine, melting at 130°-132° C. This compound is represented by the following structural formula

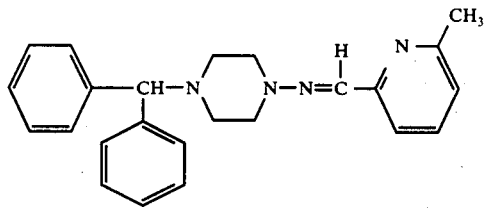

EXAMPLE 7

To 1.3 parts by weight of 1-diphenylmethyl-4-(6-methyl-2-pyridyl-methylamino)piperazine in the presence of 50 parts by volume of methanol is added 0.130 parts by weight of 5% palladium-on-carbon. This mixture is then stirred for 16 hours, filtered and concentrated to afford an oil. This oil is taken up in 4 parts by volume of ethyl ether. This solution is then seeded with a trace amount of 1-diphenylmethyl-4-(6-methyl-2-pyridylmethyleneamino) piperazine and cooled. Filtration of this solution affords as yellow crystals 1-diphenylmethyl-4-(6-methyl-2-pyridylmethyleneamino)piperazine, melting at 130°–132° C.

What I claim is:

1. A compound which is 5-diphenylmethyl-3,7-diketo-1,2-dihydro-1,2,5-triazepine.

2. A compound which is 1-diphenylmethyl-4-(6-methyl-2-pyridylmethyleneamino)-3,5-diketopiperazine.

3. A process for the preparation of 1-diphenylmethyl-4-(6-methyl-2-pyridylmethyleneamino)piperazine which comprises:
   a. Reacting iminodiacetic acid disodium salt monohydrate with thionyl chloride in the presence of ethanol with a reaction time of 20 to 72 hours to afford diethyliminodiacetate;
   b. Reacting diethyliminodiacetate with chlorodiphenylmethane at a temperature of 70°–150° C and a reaction time of 24 to 72 hours to afford diethyl-N-benzhydryliminodiacetate;
   c. Reacting diethyl-N-benzhydryliminodiacetate with hydrazine hydrate in the presence of methanol at reflux temperature and a reaction time of 20 hours to afford 5-diphenylmethyl-3,7-diketo-1,2-dihydro-1,2,5-triazepine.
   d. Reacting 5-diphenylmethyl-3,7-diketo-1,2-dihydro-1,2,5-triazepine with 6-methylpyridine-2-carboxaldehyde in the presence of benzene at reflux temperature and a reaction time of 4 hours to afford 1-diphenylmethyl-4-(6-methyl-2-pyridylmethyleneamino)-3,5-diketopiperazine;
   e. Reducing 1-diphenylmethyl-4-(6-methyl-2-pyridylmethyleneamino)-3,5-diketopiperazine using a mixture of diborane in tetrahydrofuran and boron trifluoride in diethyl ether to afford 1-diphenylmethyl-4-(6-methyl-2-pyridylmethylamino)piperazine followed by dehydrogenating to afford the desired 1-diphenylmethyl-4-(6-methyl-2-pyridylmethyleneamino)piperazine.

* * * * *